(12) United States Patent
Rabizadeh et al.

(10) Patent No.: US 9,687,491 B1
(45) Date of Patent: Jun. 27, 2017

(54) COMPOSITIONS AND METHODS OF TARGETING MUTANT K-RAS

(75) Inventors: Shahrooz Rabizadeh, Los Angeles, CA (US); Kayvan Niazi, Los Angeles, CA (US); Oleksandr Buzko, Los Angeles, CA (US); Justin Golovato, Los Angeles, CA (US); Patrick Soon-Shiong, Los Angeles, CA (US)

(73) Assignee: NantBioscience, Inc., Culver City, CA (US)

( * ) Notice: Subject to any disclaimer, the term of this patent is extended or adjusted under 35 U.S.C. 154(b) by 0 days.

(21) Appl. No.: 13/601,227

(22) Filed: Aug. 31, 2012

Related U.S. Application Data

(60) Provisional application No. 61/529,568, filed on Aug. 31, 2011.

(51) Int. Cl.
| | | |
|---|---|---|
| *A61K 38/00* | (2006.01) |
| *A61K 31/535* | (2006.01) |
| *A01N 43/40* | (2006.01) |
| *A61K 31/445* | (2006.01) |
| *A61K 31/497* | (2006.01) |
| *A01N 43/42* | (2006.01) |
| *A61K 31/47* | (2006.01) |
| *A61K 31/44* | (2006.01) |
| *A01N 43/82* | (2006.01) |
| *A61K 31/41* | (2006.01) |
| *A01N 43/90* | (2006.01) |
| *A61K 31/519* | (2006.01) |
| *A01N 43/78* | (2006.01) |
| *A61K 31/425* | (2006.01) |
| *C12N 9/96* | (2006.01) |
| *A61K 31/5377* | (2006.01) |
| *A61K 31/4245* | (2006.01) |
| *A61K 31/428* | (2006.01) |
| *A61K 31/435* | (2006.01) |
| *A61K 31/454* | (2006.01) |
| *A61K 31/4709* | (2006.01) |
| *A61K 31/496* | (2006.01) |
| *A61K 31/506* | (2006.01) |
| *A61K 31/517* | (2006.01) |
| *A61K 45/06* | (2006.01) |

(52) U.S. Cl.
CPC ........ *A61K 31/5377* (2013.01); *A61K 31/428* (2013.01); *A61K 31/4245* (2013.01); *A61K 31/435* (2013.01); *A61K 31/454* (2013.01); *A61K 31/4709* (2013.01); *A61K 31/496* (2013.01); *A61K 31/506* (2013.01); *A61K 31/517* (2013.01); *A61K 31/519* (2013.01); *A61K 45/06* (2013.01)

(58) Field of Classification Search
CPC .............. A61K 31/5377; A61K 31/428; A61K 31/435; A61K 31/4245; A61K 31/4709; A61K 31/506; A61K 31/519; A61K 31/545; A61K 45/06; A61K 31/496; A61K 31/517
See application file for complete search history.

(56) References Cited

PUBLICATIONS

Ekins et al "In silico pharmacology for drug discovery: applications to targets and beyond" Brit J Pharamcol 152:21-37. Published online Jun. 4, 2007.*
Monticone et al. "Gene expression deregulation by KRAS G12D and G12V in a BRAF V600E context" Molecular Cancer 7:92-104. Published 2008.*
Elad-Sfadia et al. "Galectin-1 Augments Ras Activation and Diverts Ras Signals to Raf-1 at the Expense of Phosphoinositide 3-Kinase" J. Biol. Chem. 277:37169-37175. Published Jul. 30, 2002.*
Grant, Barry J., "Novel Allosteric Sites on Ras for Lead Generation," PLos One, vol. 6, Issue 10, Oct. 2011; pp. 1-10.
Hornak, Viktor, et al., "Comparison of Multiple Amber Force Fields and Development of Improved Protein Backbone Parameters," Proteins: Structure, Function and Bioinformatics 65:712-725 (2006).

* cited by examiner

*Primary Examiner* — Christina Bradley
*Assistant Examiner* — Zachary J Miknis
(74) *Attorney, Agent, or Firm* — Fish & Tsang, LLP

(57) ABSTRACT

The invention relates to a method of modeling K-Ras proteins with one or more mutations that result in constitutive activity, and identifying compounds that inhibit interactions among activated K-Ras proteins and their upstream and downstream effectors.

1 Claim, 7 Drawing Sheets

K-Ras Sequence

Nucleotide Sequence (567 nt):

ATGACTGAATATAAACTTGTGGTAGTTGGAGCTGGTGGCGTAGGCAAGAGTGCCTTGAC
GATACAGCTAATTCAGAATCATTTTGTGGACGAATATGATCCAACAATAGAGGATTCCTAC
AGGAAGCAAGTAGTAATTGATGGAGAAACCTGTCTCTTGGATATTCTCGACACAGCAGGT
CAAGAGGAGTACAGTGCAATGAGGGACCAGTACATGAGGACTGGGGAGGGCTTTCTTTG
TGTATTTGCCATAAATAATACTAAATCATTTGAAGATATTCACCATTATAGAGAACAAATTA
AAAGAGTTAAGGACTCTGAAGATGTACCTATGGTCCTAGTAGGAAATAAATGTGATTTGC
CTTCTAGAACAGTAGACACAAAACAGGCTCAGGACTTAGCAAGAAGTTATGGAATTCCTT
TTATTGAAACATCAGCAAAGACAAGACAGGGTGTTGATGATGCCTTCTATACATTAGTTCG
AGAAATTCGAAAACATAAAGAAAAGATGAGCAAAGATGGTAAAAAGAAGAAAAAGAAGTC
AAAGACAAAGTGTGTAATTATGTAA

Translation (188 aa):

MTEYKLVVVGAG◯VGKSALTIQLIQNHFVDEYDPTIEDSYRKQVVIDGETCLLDILDTAG◯EEY
SAMRDQYMRTGEGFLCVFAINNTKSFEDIHHYREQIKRVKDSEDVPMVLVGNKCDLPSRTVD
TKQAQDLARSYGIPFIETSAKTRQGVDDAFYTLVREIRKHKEKMSKDGKKKKKSKTKCVIM

Figure 3B

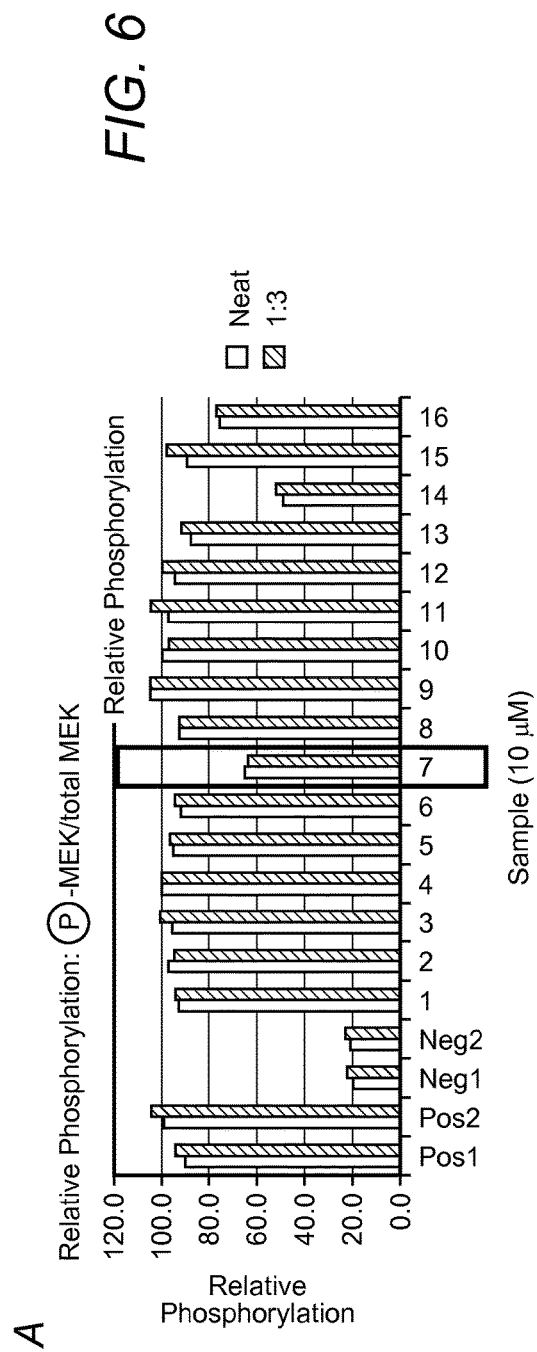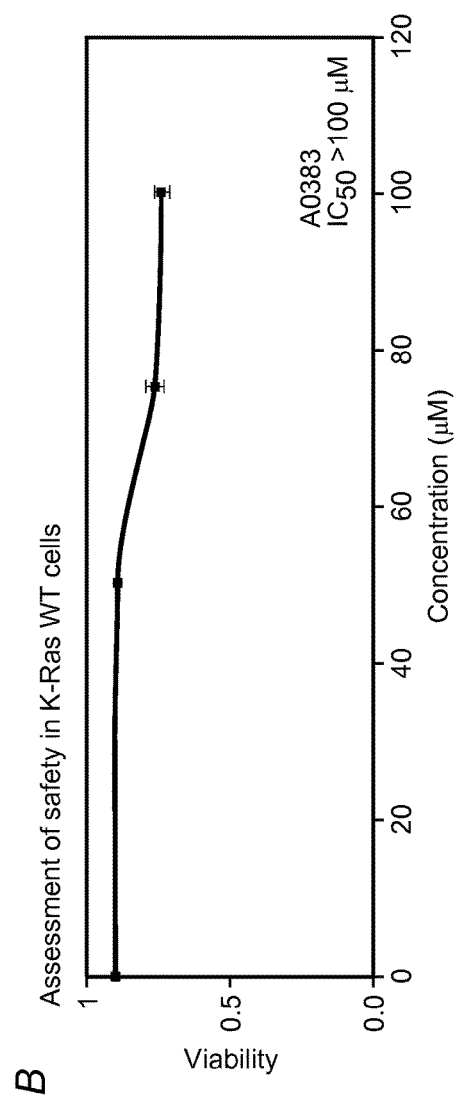
FIG. 6

SEQUENCE LISTING

```
<160> NUMBER OF SEQ ID NOS: 2

<210> SEQ ID NO 1
<211> LENGTH: 567
<212> TYPE: DNA
<213> ORGANISM: Homo sapiens

<400> SEQUENCE: 1
atgactgaat ataaacttgt ggtagttgga gctggtggcg taggcaagag tgccttgacg      60
atacagctaa ttcagaatca ttttgtggac gaatatgatc caacaataga ggattcctac     120
aggaagcaag tagtaattga tggagaaacc tgtctcttgg atattctcga cacagcaggt     180
caagaggagt acagtgcaat gagggaccag tacatgagga ctggggaggg ctttctttgt     240
gtatttgcca taaataatac taaatcattt gaagatattc accattatag agaacaaatt     300
aaaagagtta aggactctga agatgtacct atggtcctag taggaaataa atgtgatttg     360
```

```
ccttctagaa cagtagacac aaaacaggct caggacttag caagaagtta tggaattcct    420
tttattgaaa catcagcaaa gacaagacag ggtgttgatg atgccttcta tacattagtt    480
cgagaaattc gaaaacataa agaaagatg agcaaagatg gtaaaagaa gaaaaagaag     540 tcaaagacaa agtgtgtaat tatgtaa                                        567
```

```
<210> SEQ ID NO 2
<211> LENGTH: 188
<212> TYPE: PRT
<213> ORGANISM: Homo sapiens

<400> SEQUENCE: 2

Met Thr Glu Tyr Lys Leu Val Val Gly Ala Gly Val Gly Lys
1               5                  10                 15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

US 9,687,491 B1

COMPOSITIONS AND METHODS OF TARGETING MUTANT K-RAS

This application claims the benefit of priority to U.S. Provisional Application Ser. No. 61/529,568 filed on Aug. 31, 2011. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The described invention relates to computational investigation of the structure of mutant K-Ras to permit rational design and discovery of compounds that specifically cause the destruction of cancer cells bearing constitutively-activating mutations in K-Ras. More specifically, the invention relates to the discovery of a novel structural feature formed in K-Ras mutants and is targeted to inhibit the activity of the mutant proteins.

BACKGROUND OF THE INVENTION

K-Ras (or Ki-Ras or Kirsten-Ras) is a 21 kD member of the Ras family of GTPase proteins. Genetic alterations in the genome encoding for K-Ras are associated with development of neoplasia. Approximately 33% of all human tumors express mutant Ras, these mutations often stabilize Ras in GTP-bound (active) state. Mutations found in K-Ras associate strongly with pancreatic cancer (90%), biliary tract cancer (33%), colorectal cancer (32%), and lung cancer (20%), among others. Approximately 20-25% of all human tumors harbor an activating mutation in gene encoding K-Ras. Examples of cancer-associated mutations are found at glycine-12 (Gly12), Gly13, and glutamine-61 (Gln61), with Gly12 being the predominant site of mutagenesis (88%).

Cancer-associated mutant K-Ras is constitutively active, with prolonged stabilization of its GTP-bound (active) state, and is thus able to constitutively activate downstream client effectors such as Raf kinase and phosphoinositide-3 kinase (PI3K). Both of these kinases play important roles in proliferation/survival/anti-apoptotic signaling pathways. These mutations have been implicated in insensitivity to EGFR-targeted anti-cancer therapies as mutations in K-Ras predispose cancer cells to be significantly less responsive to EGFR targeting therapies (e.g., Panitumumab, Cetuximab, etc.). Interaction with the Ras GTPase activating protein (Ras-GAP) is vital to the timely inactivation of K-Ras, resulting in more efficient hydrolysis of GTP to GDP. The conformational changes in K-Ras structure stemming from GTP hydrolysis result in the elimination of K-Ras' affinity for effector proteins, thereby inactivating downstream proliferation and anti-death pathways. Cancer-associated mutations in K-Ras have been shown to interact poorly with RasGAP, therefore remaining in the "on" or constitutively active position.

In view of the important role K-Ras plays in various neoplastic disease states, it would be advantageous to be able to identify compounds that bind specifically to the mutant K-Ras protein forms associated with cancer diseases states.

SUMMARY OF THE INVENTION

The present invention is drawn to compounds, compositions, and methods of formation of complexes of a mutant K-Ras protein with a ligand. In especially preferred aspects, ligands and complexes are therapeutically effective in the treatment of disorders that are associated with mutant K-Ras protein.

In one aspect of the inventive subject matter, the complex comprises a K-Ras protein (SEQ ID NO:1) with a G12V substitution, wherein the protein with the G12V substitution has a first and a second conformation, wherein the first conformation has a linear I-groove spanning residues Glu91, Asp92, Tyr96, Ala11, Gly60, Ala59, Thr35, Pro34, and Ile36, and wherein the second conformation has a branched Y-groove spanning Asp92, Ala11, Gln61, Glu62, Gly60, Ala59, Thr35, Arg68, Thr58, Tyr71 and Ile36, and wherein the compound binds specifically with the linear I-groove or Y-groove to form the complex. It is particularly preferred that the linear I-groove further comprises a plurality of flanking residues selected from the group consisting of Gln61, Lys88, Val12, Glu62, and Tyr32, and that the branched Y-groove comprises a selection of residues that includes Gln61, Ala11, Glu62, Ile36, Tyr71, Val12, Pro34 and Thr35. It is also contemplated that the complex further comprises one molecule of guanosine triphosphate (GTP) or analog thereof, typically with the groove encompassing the γ-phosphate of the GTP molecule. It is still further preferred that the complex is incapable of activating c-Raf or phosphoinositide 3-kinase (PI 3-kinase).

In particularly preferred complexes, the compound is selected from the group consisting of: 1-[4-(4-{[2-(1H-imidazol-4-yl)ethyl]amino}piperidin-1-yl)phenyl]pyrrolidin-2-one, 2-{[4-(4-acetylphenyl)piperazin-1-yl]methyl}-3H-quinazolin-4-one, 1-methyl-3-[4-(4-{[2-(2-methylimidazol-1-yl)ethyl]amino}piperidin-1-yl)phenyl] imidazolidin-2-one, 1-(2H-1,3-benzodioxol-5-ylmethyl)-4-[(3S)-1-(1H-imidazol-4-ylmethyl)piperidin-3-yl]piperazine, 6-(aminomethyl)-2-(3-{[4-(pyrazol-1-ylmethyl)piperidin-1-yl]methyl}phenyl)-3H-pyrimidin-4-one, (4R)—N-[(6-chloroquinolin-2-yl)methyl]-1-(pyridin-2-yl)-4,5,6,7-tetrahydroindazol-4-amine, (3R,4R)-4-[4-(pyridin-2-yl)piperazin-1-yl]-1-(pyridin-2-ylmethyl)piperidin-3-ol, 7-{[4-(4-acetylphenyl)piperazin-1-yl]methyl}pyrimido[2,1-b][1,3] thiazol-5-one, 3-[(E)-{[3-(2,3-dihydro-1,4-benzodioxin-6-yl)-1-phenylpyrazol-4-yl]methylidene}amino]-8-methyl-1,3-diazaspiro[4.5]decane-2,4-dione, 1-(4-amino-1,2,5-oxadiazol-3-yl)-5-[4-(hydroxynitroso)phenyl]-N'-[(1E,2E)-3-phenylprop-2-en-1-ylidene]-1,2,3-triazole-4-carbohydrazide, 3-({12-[4-(furan-2-ylcarbonyl)piperazin-1-yl]-8-oxo-15-oxa-14-azatetracyclo[7.6.1.0^{2,7}.0^{13,16}]hexadeca-1(16),2(7),3,5,9,11,13-heptaen-10-yl}amino) benzoic acid, 4-chloro-N-[(7S)-7-(4-fluorophenyl)-5-phenyl-4H,7H-[1,2,4]triazolo[1,5-a]pyrimidin-2-yl] benzenesulfonamide, (5S)-4-(2,3-dihydro-1,4-benzodioxin-6-ylcarbonyl)-5-(4-ethylphenyl)-3-hydroxy-1-(6-methyl-1,3-benzothiazol-2-yl)-5H-pyrrol-2-one, (5S)-1-(6-chloro-1,3-benzothiazol-2-yl)-4-(2,3-dihydro-1,4-benzodioxin-6-ylcarbonyl)-3-hydroxy-5-[4-(hydroxynitroso)phenyl]-5H-pyrrol-2-one, O-{[4-({4-[(2E)-2-[(3-fluorophenyl) methylidene]hydrazin-1-yl]-6-(morpholin-4-yl)-1,3,5-triazin-2-yl}amino)phenyl]nitroso}oxidanol, (2E)-3-(1,5-dimethyl-3-oxo-2-phenylpyrazol-4-yl)-5-[(3Z)-2-oxo-1H-indol-3-ylidene]-2-{2-[(3E)-2-oxo-1H-indol-3-ylidene] hydrazin-1-ylidene}-1,3-thiazolidin-4-one, 5-(5-{[(4Z)-5-oxo-1,3-diphenylpyrazol-4-ylidene]methyl}furan-2-yl)-2H-isoindole-1,3-dione, 5-[(6S)-5-benzyl-1H,4H,6H,7H-imidazo[4,5-c]pyridin-6-yl]-3-(pyridin-2-yl)-1,2,4-oxadiazole, 2-(hydroxynitroso)-6-[(1E)-(2-{4-[(4-methylphenyl)amino]-6-(morpholin-4-yl)-1,3,5-triazin-2-yl}hydrazin-1-ylidene)methyl]phenol, (7'S)-12'-({[(5E)-1- methyl-2,4,6-trioxo-1,3-diazinan-5-ylidene]methyl}amino)-5'-phenyl-2',5'-diazaspiro[1,5-diazinane-3,8'-tricyclo [8.4.0.0^{2,7}]tetradecane]-1'(14'),10',12'-triene-2,4,6-trione, 4-[(10R,10aR)-7,7-dimethyl-9,11-dioxo-6H,8H, 10H,10aH-indeno[1,2-b]quinolin-10-yl]phenyl 4-acetamidobenzenesulfonate, (5S)-1-(6-chloro-1,3-benzothiazol-2-yl)-4-(2,3-dihydro-1,4-benzodioxin-6-ylcarbonyl)-3-hydroxy-5-[3-(hydroxynitroso)phenyl]-5H-pyrrol-2-one, (5S)-4-(2,3-dihydro-1,4-benzodioxin-6-ylcarbonyl)-3-hydroxy-5-[3-(hydroxynitroso)phenyl]-1-(6-methyl-1,3-benzothiazol-2-yl)-5H-pyrrol-2-one, N-cyclooctyl-3-[(4-fluorobenzene)sulfonamido]-4-[(1S,9R)-6-oxo-7,11-diazatricyclo[7.3.1.0^{2,7}]trideca-2,4-dien-11-yl] benzamide, O-[(3-{[4,6-bis(1,2,3-benzotriazol-1-yl)-1,3,5-triazin-2-yl]amino}phenyl)nitroso]oxidanol, N-[4-({5,7-diphenyl-[1,2,4]triazolo[1,5-a]pyrimidin-2-yl}sulfamoyl)phenyl]acetamide, 3-({8-oxo-12-[4-(pyridin-2-yl)piperazin-1-yl]-15-oxa-14-azatetracyclo[7.6.1.0^{2,7}.0^{13,16}] hexadeca-1(16),2(7),3,5,9,11,13-heptaen-10-yl}amino) benzoic acid, and 1-(4-amino-1,2,5-oxadiazol-3-yl)-N'-[(1Z)-3,4-dihydro-2H-naphthalen-1-ylidene]-5-phenyl-1,2,3-triazole-4-carbohydrazide.

In another aspect of the inventive subject matter, the complex comprises a K-Ras protein (SEQ ID NO:1) with a G12D substitution, wherein the protein has a conformation that comprises a groove spanning residues Asp12, Ala59, Thr35, Asp57, Met67, Ile36, Ser39, Leu56, Thr58, Lys5, Lys16, Asp38, Val7 and Asp54, and a compound that binds specifically with the groove to form the complex.

In a further aspect of the inventive subject matter, the complex comprises a K-Ras protein (SEQ ID NO:1) with a G12C substitution, wherein the protein has a conformation that comprises a groove spanning residues Cys12, Gln61, Glu62, Ala59, Gly60, Met67, Thr35, Ile36, Pro34, Tyr32, and a compound that binds specifically with the groove to form the complex.

In a still further aspect of the inventive subject matter, the inventors also contemplate a method of identifying Ras effector interaction inhibitor compounds. Preferred methods include a step of providing a mutant K-Ras protein, a step of forming a complex between a candidate compound and a groove of the mutant K-Ras protein; and a further step of determining the complex for binding affinity to a Ras effector, whereby the candidate compound that forms the complex with a reduced binding affinity to the Ras effector is a Ras effector interaction inhibitor. In especially preferred methods, the mutant K-Ras protein comprises a G12V, G12D, or G12C mutation, and/or the Ras effector is a downstream effector (e.g., b-Raf, c-Raf or a PI 3-kinase). Alternatively, the Ras effector is an upstream effector (e.g., EGFR or VEGFR). Suitable mutant proteins may be provided as an in silico construct (preferably achieving conformational stability after approximately 5 nanoseconds), or may be derived from a cancer associated with constitutive K-Ras activity (e.g., biliary tract, bladder, breast, cervix, endometrial, kidney, large intestine, liver, lung, melanoma, myeloid leukemia, ovarian, pancreas, and thyroid cancer).

Viewed from a different perspective, the inventors also contemplate a method of forming a complex with a mutant K-Ras protein. Such methods will preferably include a step of identifying a structural feature as a binding site in the mutant K-Ras protein, wherein the structural feature is selected from the group consisting of (a) a groove spanning residues Glu91, Asp92, Tyr96, Ala11, Gly60, Ala59, Thr35, Pro34, and Ile36, (b) a groove spanning Asp92, Ala11, Gln61, Glu62, Gly60, Ala59, Thr35, Arg68, Thr58, Tyr71 and Ile36 (c) a groove spanning residues Cys12, Gln61, Glu62, Ala59, Gly60, Met67, Thr35, Ile36, Pro34, Tyr32, and (d) a groove spanning residues Asp12, Ala59, Thr35, Asp57, Met67, Ile36, Ser39, Leu56, Thr58, Lys5, Lys16, Asp38, Val7 and Asp54. In yet another step, a potential ligand is calculated for the structural feature by minimizing fee energy of the potential ligand to achieve a threshold value, and in a further step, the potential ligand is synthesized/obtained and combined with the mutant K-Ras protein to thereby form the complex. Most preferably, the mutant K-Ras protein is a K-Ras protein (SEQ ID NO:1) with a G12V substitution, a K-Ras protein (SEQ ID NO:1) with a G12D substitution, or a K-Ras protein (SEQ ID NO:1) with a G12C substitution.

Therefore, the inventors also contemplate a pharmaceutical composition that includes a pharmaceutically acceptable carrier and a mutant K-Ras protein ligand that binds to a groove selected from the group consisting of (a) a groove spanning residues Glu91, Asp92, Tyr96, Ala11, Gly60, Ala59, Thr35, Pro34, and Ile36, (b) a groove spanning Asp92, Ala11, Gln61, Glu62, Gly60, Ala59, Thr35, Arg68, Thr58, Tyr71 and Ile36 (c) a groove spanning residues Cys12, Gln61, Glu62, Ala59, Gly60, Met67, Thr35, Ile36, Pro34, Tyr32, and (d) a groove spanning residues Asp12, Ala59, Thr35, Asp57, Met67, Ile36, Ser39, Leu56, Thr58, Lys5, Lys16, Asp38, Val7 and Asp54; wherein the mutant K-Ras protein ligand is present at a concentration effective to form a mutant K-Ras protein ligand complex in vivo.

While not limiting to the inventive subject matter, it is further preferred that the pharmaceutical composition will also include a second pharmaceutically active compound (e.g., a cytostatic or cytotoxic compound), and/or a Ras inhibitor, a Raf inhibitor, a PI3K inhibitor, or a compound that re-activates p53 activity.

Consequently, the inventors also contemplate a method of treating a patient diagnosed with a neoplastic disease that is characterized by a mutant K-Ras protein, wherein the method includes a step of administering to the patient contemplated pharmaceutical compositions, typically at a dosage and under a protocol to induce cell death in a cell containing the mutant K-Ras protein.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 6 illustrates the reduction of phosphorylation of MEK1 by compound A0383 (2-(hydroxynitroso)-6-[(1E)-(2-{4-[(4-methylphenyl)amino]-6-(morpholin-4-yl)-1,3,5-triazin-2-yl}hydrazin-1-ylidene)methyl]phenol) in 293 cells overexpressing K-Ras G12V. In (A), 10 M treatment with A0383 (sample 7) significantly reduced phosphorylation of MEK1 in an ultra-sensitive immunoassay. (B) illustrates the lack of general toxicity in 293 cells (not overexpressing mutant K-Ras) in dosages of A0383 ranging from 50-100 M.

DETAILED DESCRIPTION OF THE INVENTION

Figure 1:
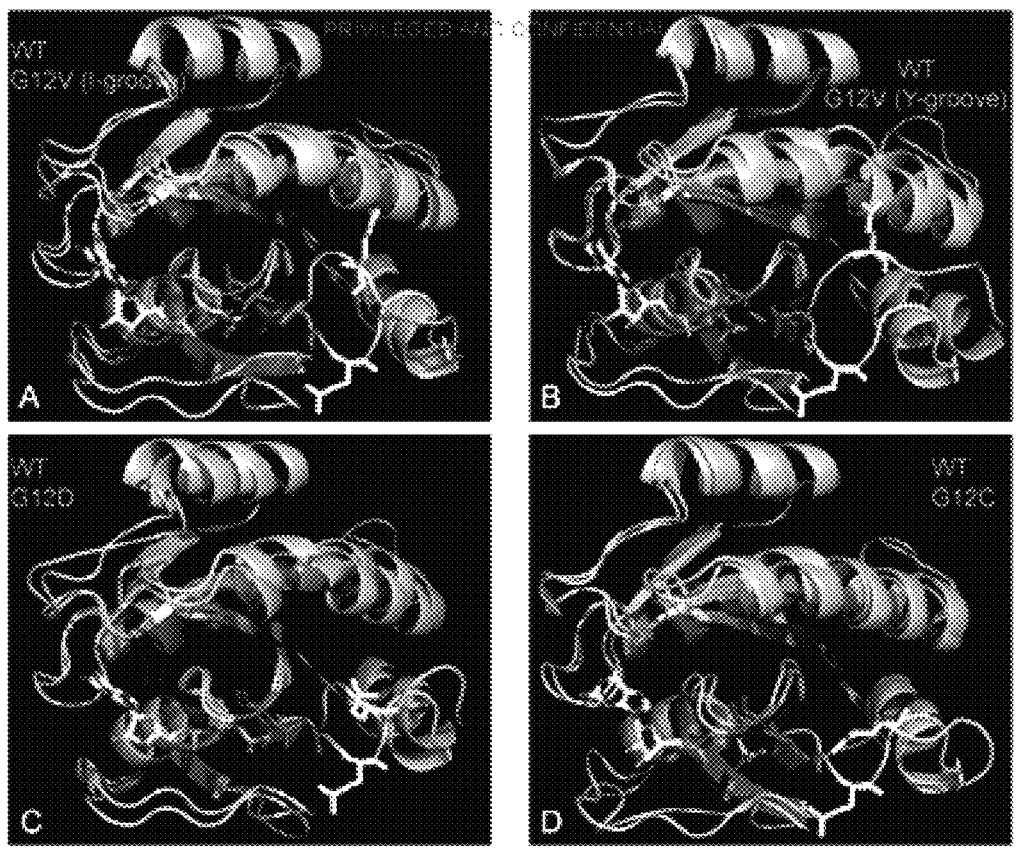
FIG. 1 shows overlays of ribbon structures of molecular models of wild type K-Ras and K-Ras mutants. In each Figure, the amino acid glycine located at position 12 (highlighted in dark gray) in wild type K-Ras has been mutated to valine (A-B), aspartate (C), or cysteine (D) in the overlay; glutamine at position 61 (white) is highlighted to illustrate the impact of mutations at position 12 on K-Ras' tertiary structure. Overlays of the wild type and G12V "I-groove" and G12V "Y-groove" structures are shown in (A) and (B), respectively. As illustrated in the Figure, the structures of the mutant and wild type proteins remains relatively well-aligned, with the exception of the residues in the so-called switch II region of K-Ras (residues 60-77), in which mutations at the distant Gly12 alter the geometrical positioning of the switch II amino acids, including Gln61. The positioning of Gln61 is thought to be important for interaction between KRas and RasGAP, the protein that facilitates inactivation of K-Ras.

The presently described invention relates to the discovery of a structural feature present in mutant K-Ras proteins that was previously unreported. This structural feature provides a target against which candidate compounds are designed and screened, using computational and other screening methods.

The methods disclosed here use computational modeling of mutant K-Ras proteins to identify structural differences existing among wild type and mutant K-Ras proteins. Examples of cancer-associated mutations are found at glycine-12 (Gly12), Gly13, and glutamine-61 (Gln61). Any of these mutations, whether taken alone or in combination with one another, can be used as the basis of an in silico model of mutant K-Ras proteins. Once one or more structural differences present in the mutant K-Ras proteins are identified, computational methods are then utilized to identify compounds that bind to the specific structural feature. Alternatively, screening of compound libraries can be used to identify compounds of interest.

A candidate compound is one that prevents or inhibits the binding of an activated K-Ras protein or a mutant K-Ras protein with one or more upstream or downstream effector proteins. Examples of upstream effectors include the epithelial growth factor receptor (EGFR), platelet-derived growth factor receptor (PDGFR), and the vascular endothelial growth factor receptor (VEGFR). Examples of downstream effectors include b-Raf and c-Raf (Raf-1) which are serine/threonine-specific kinases and play a role in the MAPK/ERK signal transduction pathway, or a phosphoinositide 3-kinase (PI 3-kinase).

Modeling

To date, the reported results of X-ray analysis of crystallized wild type and mutant K-Ras have not shown significant structural differences existing between these forms of the protein. Because the static structures of the crystallized proteins failed to indicate structural differences associated with the different functions of these proteins, alternative methods were employed, the results of which are discussed here.

A molecular dynamics (MD) approach was used to explore the structures of the wild type and mutant K-Ras proteins. This approach resulted in determining the predominant conformations of the wild type and G12V, G12C, and G12D mutant K-Ras proteins. It should be noted that any other mutation in the K-Ras amino acid sequence that produces constitutive activity can also be used, whether alone or in combination with other mutations, with the methods disclosed herein. The results of this analysis identified structural differences between the two proteins that explain the observed differences in functional behavior.

The molecular dynamics program Amber 11 was used for this structural analysis. The program is used to generate or provide in silico structures of the mutant and wild type proteins. Amber 11 models the dynamic behavior of the in silico protein structures by calculating the direction and magnitude of atomic forces acting on individual atoms, thereby providing a view of the conformational changes over biologically relevant periods of time. Typically, structural conclusions can be made based on 20-50 nanoseconds of simulated time, depending on the size and complexity of the system under study. A series of simulations was run using the backbone conformation of the wild type K-Ras as the starting point. The G12V mutant structure was obtained from that of the wild type protein by replacing the side chain of Gly12 using molecular graphics software. The Amber FF99SB force field was used to simulate both proteins in explicit water. Modeling a protein in an explicitly defined volume of water molecules gives the best possible accuracy, since it avoids the approximations that are made by continuum solvent models that treat water as a continuous medium.

Using the described software and force field, the wild type and the G12V, G12D, and G12C mutants of K-Ras were simulated for over 500 nanoseconds in several separate molecular dynamics simulations. Since each simulation potentially explores conformational space along a different path, it is important to run several of them to maximize conformational space coverage. Subsequent cluster analysis was used to group observed protein conformations according to mutual similarity. Finally, representative structures were analyzed from the most abundant clusters. These structures correspond to the most common conformations of each protein.

The overall structures of the wild type and the G12V, G12D, and G12C mutant K-Ras were almost identical. However, notable differences were detected in the region of a flexible loop spanning residues 60 through 77 and frequently referred to as Switch II. The structures of the mutant and wild type proteins are provided as overlays in FIG. 1 for direct comparison. This Switch II loop is highly sensitive to local structural changes, including presence of GTP or GDP. The inherent flexibility of Switch II allows it to modulate properties of the surface used by K-Ras to bind its downstream effector proteins. In addition, residue Gln61 located within Switch II has been implicated in the process of K-Ras inactivation by Ras GTPase activating protein (RasGAP). The Gln61 residue of the wild type protein appears to provide charge stabilization for the interaction with Lys789 of RasGAP that is required for a stable K-Ras/RasGAP complex. With the complex correctly formed, GTP becomes replaced with GDP, which inactivates Ras. However, G12V mutation of K-Ras introduces a bulky valine side chain, which prevents the Gln61 from maintaining its proper conformation.

Figure 2:
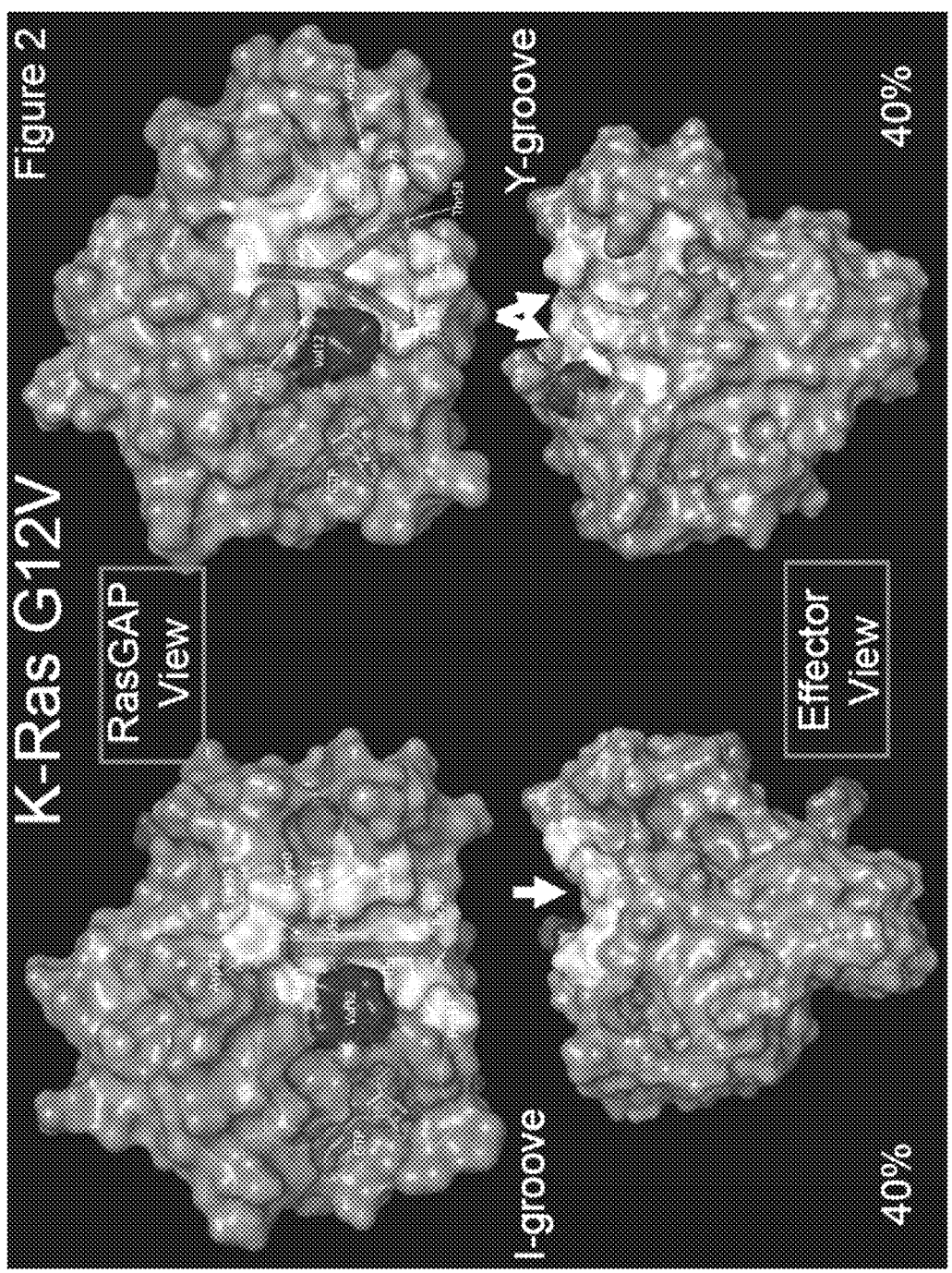
FIG. 2 shows surface rendering of molecular models of the "Y-groove" and "I-groove" structures formed by the G12V mutant form of K-Ras, both annotated to highlight amino acids that line the newly discovered grooves. The arrows indicate the locations of the 'druggable' grooves discovered to be specifically present in the G12V mutant. The RasGAP view represents the area of interaction between K-Ras and RasGAP, the protein responsible for the inactivation of K-Ras via hydrolysis of GTP to GDP. The Effector view represents the area of interaction between K-Ras and its effector proteins (e.g., PI-3K, Raf, etc.).

Extensive molecular dynamics simulations revealed the exact nature of the resulting conformational changes. The mutant protein exists in two predominant forms, which together account for approximately 80% of the total simulated time. These two conformations differ from the wild type by the presence of a deep groove in the surface adjacent to the mutation site. One of the mutant conformations features a linear groove that runs from Asp92 to Thr35 at the edge of the surface interface with b-Raf, PI3K, etc. (FIG. 2). This structural feature is referred to as the I-groove to reflect its geometry. The other conformation of the mutant K-Ras is similar to the I-groove conformation, but differs from it by a branching element in the surface groove that is directed toward Glu37. Since this feature has a branched topology, it was termed the Y-groove. None of these changes were observed in the simulations of the wild type protein. In addition, the wild type K-Ras remained completely stable for over 50 nanoseconds of simulated time.

The openings of both the I- and Y-grooves formed in the G12V mutant K-Ras are located on the edge of the surface of the protein responsible for binding of its effectors. Notably, two of the residues required for PI3K binding (Asp33 and Ile36) are located in the immediate proximity to the groove openings. This structural feature made it possible to simultaneously and specifically bind mutant K-Ras G12V and inhibit the interaction between K-Ras G12V and PI3K, effecting the demise of cancer cells expressing K-Ras G12V.

Figure 3:
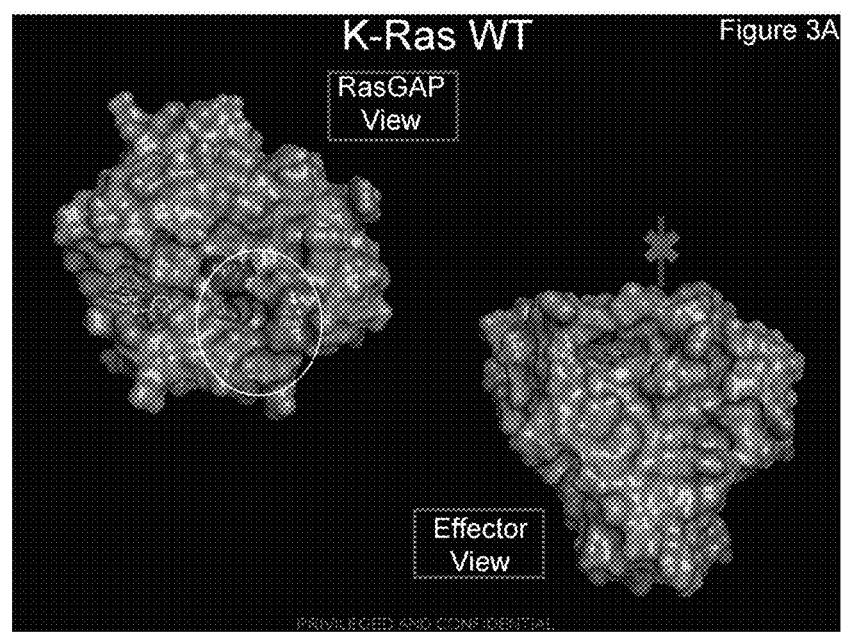
FIG. 3A shows surface rendering of molecular models of the wild type form of KRas, with the yellow oval indicating areas consisting of amino acid residues which prohibit groove formation in the wild type. The arrow indicates the location of the 'druggable' groove discovered to be specifically present in the mutant K-Ras and absent in the wild type. The nucleotide and amino acid sequences for wild type K-Ras are shown in FIG. 3B (dark gray: Gly12, light gray: Gly13, medium gray: Gln61).

FIG. 2 shows side and top down views, of the I-groove and Y-groove structures formed by G12V mutant K-Ras with GTP bound (indicated in yellow). The I-groove on the surface of K-Ras G12V is defined by Glu91, Asp92, Tyr96, Ala11, Gly60, Ala59, Thr35, Pro34, and Ile36. It is also bounded by Gln61, Lys88, Val12 and Glu62. The Y-groove is outlined by Asp92, Ala11, Gln61, Glu62, Gly60, Ala59, Thr35, Arg68, Thr58, Tyr71. The side chain of Ile36 serves as the divider between the two branches of the Y-groove. In comparison, FIG. 3 shows a side view and a top view of the wild type protein. Without wishing to be bound by theory, it appears that the side chains of Gly12, Gln61 and other residues in the area of the groove serve to protect or prevent the groove from forming. Accordingly, mutation of other residues in this general area of the K-Ras protein may give rise to other constitutively active K-Ras variations.

Molecular dynamics simulations that were used for modeling of the G12V mutant of K-Ras can be used equally successfully to model other mutants of this protein. We have carried out a series of simulations of other mutated variants of K-Ras predominant in a variety of human tumors, including G12C and G12D.

Each in silico protein structure was prepared by using the backbone of the wild type K-Ras and replacement of the side chain in question. Simulations were run for 50 ns and each produced several dominant conformations, which differ from the structure of the wild type K-Ras.

Figure 4:
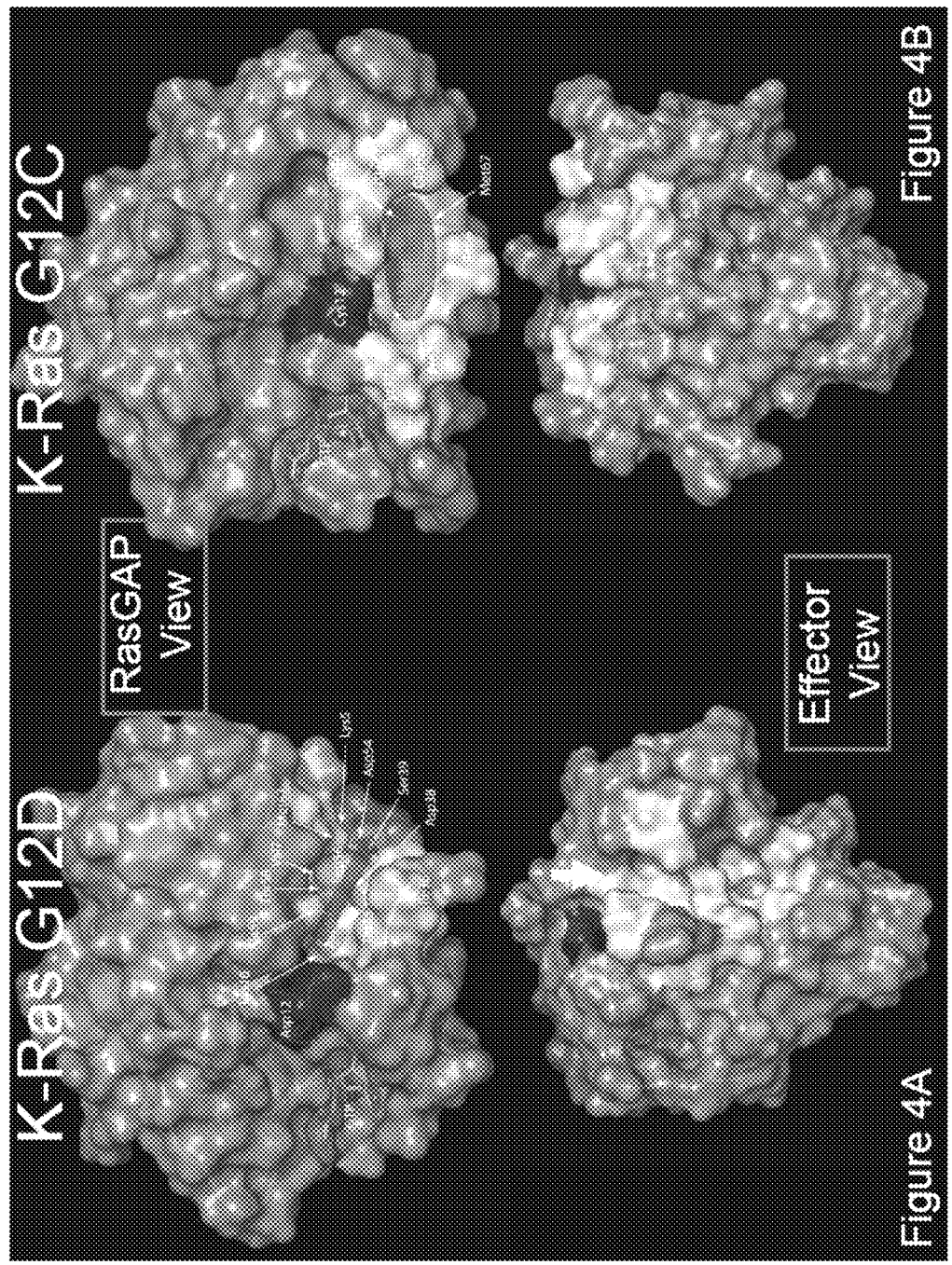
FIG. 4 shows surface rendering of molecular models of A) K-Ras G12D and B) K-Ras G12C, both annotated to illustrate amino acids that line the newly discovered groove and pocket, respectively. The arrows in (A) and the oval shading in (B) indicate the locations of the 'druggable' areas discovered to be specifically present in the G12D and G12C mutants, respectively.

The G12D mutant of K-Ras developed a deep groove spanning its surface away from the GTP binding site along the effector binding surface (FIG. 4A). The residues that define this groove are Asp12, Ala59, Thr35, Asp57, Met67, Ile36, Ser39, Leu56, Thr58, Lys5, Lys16, Asp38, Val7 and Asp54. Due to its close proximity to the effector binding surface, this groove represents a suitable target for computational discovery of active compounds targeting specifically the G12D mutant of K-Ras.

The G12C mutant features a similar structural element, which differs in its overall geometry, but is located in approximately the same part of the protein structure (FIG. 4B). The wider and more defined pocket of the G12C mutant occupies the following residues: Cys12, Gln61, Glu62, Ala59, Gly60, Met67, Thr35, Ile36, Pro34, Tyr32. It also is flanked by the GTP molecule. The overall shape and location of this pocket presents an opportunity to specifically target the G12C mutant of K-Ras.

The model system described above is equally applicable to other constitutively active mutations of K-Ras, including, but not limited to, G12R, G12S, G12A, G13D, G13C, Q61H, Q61L, and Q61R.

Contemplated Compounds

The methods described herein have yielded a number of compounds that have been modeled to interact with the groove in the mutant K-Ras protein G12V. Molecular docking software was used to facilitate discovery of compounds capable of binding the described I- and Y-grooves and blocking the interaction of Asp33 and Ile36 with PI3K. Molecular docking was based on the two dominant conformations of K-Ras produced by our molecular dynamics simulations and led to the discovery of novel compounds that specifically bind mutant K-Ras G12V, do not efficiently bind wild type K-Ras, and disrupt the interaction of K-Ras G12V with PI3K.

Molecular docking simulations started with ~1 million compounds selected from a larger set to satisfy the constraints of size, functionality and physical properties. The initial docking has produced a set of protein-ligand complexes ranked by estimated affinity. This stage was followed by a high accuracy scoring approach based on molecular dynamics and referred to as MM-PBSA (Molecular Mechanics-Poisson-Boltzmann Surface Area). MM-PBSA offers the possibility of simulating a dynamic sequence of states for each complex in aqueous solution. Each protein-ligand complex was simulated by molecular dynamics in explicit water, and statistical analysis of the structure was performed. MM-PBSA scores were then used to improve the accuracy of compound ranking and select candidates for experimental testing.

Figure 5:
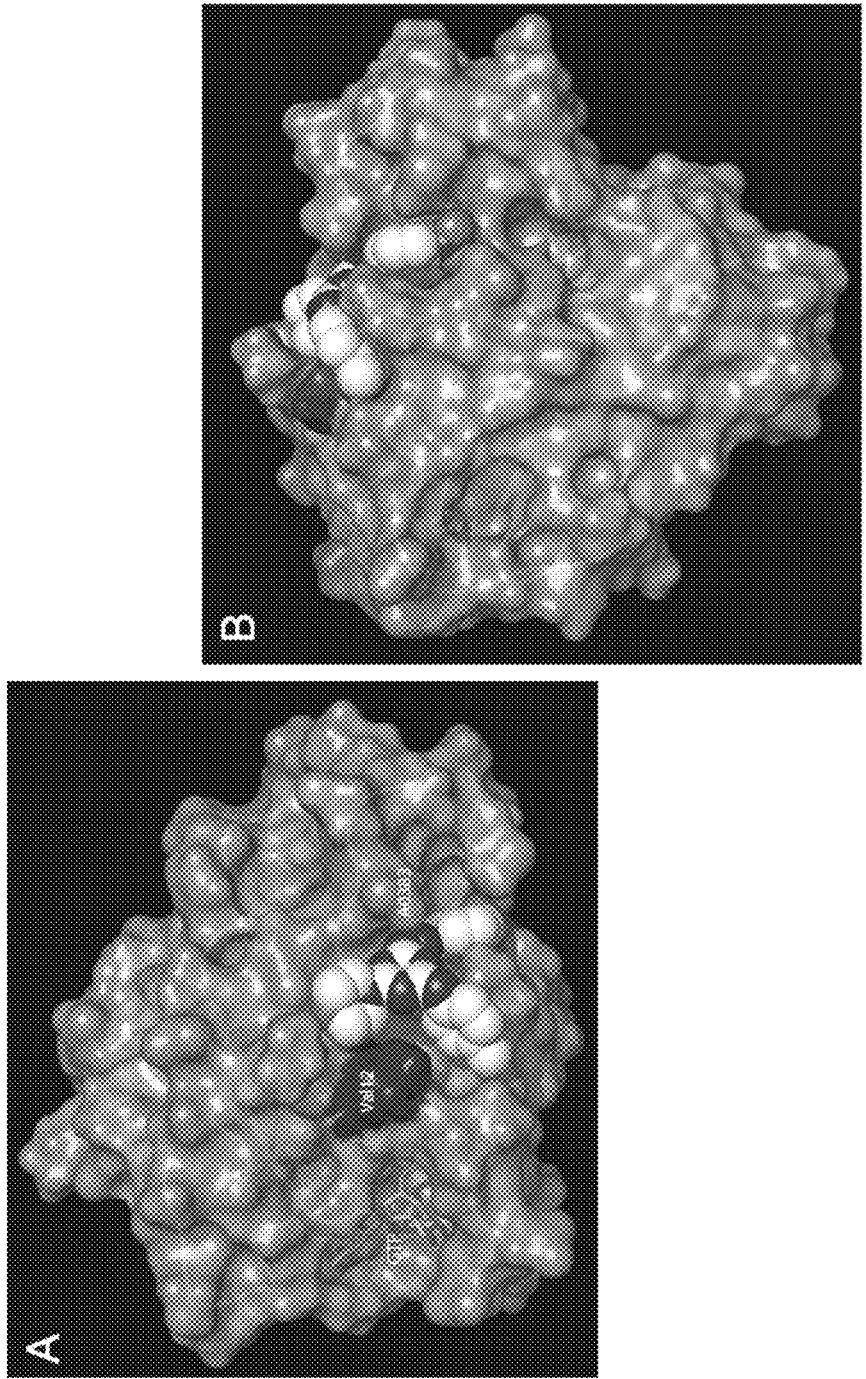
FIG. 5 shows a RasGAP view (A) and an Effector view (B) of a surface rendering of a sample model of a G12V mutant K-Ras with a bound molecule of GTP and a candidate compound (A0383).

An illustration of a typical modeling experiment is shown in FIGS. 5A and 5B. These drawings show the mutant G12V K-Ras protein with Val12 in dark red. A candidate compound is colored by element (carbon is gray, oxygen is red, and nitrogen is blue), and a molecule of GTP is shown in orange.

Some of the discovered compounds are presented:

| Compound Name | Structure | Score |
|---|---|---|
| 1-[4-(4-{[2-(1H-imidazol-4-yl)ethyl]amino}piperidin-1-yl)phenyl]pyrrolidin-2-one<br>Reference # A0158 | | |
| 2-{[4-(4-acetylphenyl)piperazin-1-yl]methyl}-3H-quinazolin-4-one<br>A0190 | | |
| 1-methyl-3-[4-(4-{[2-(2-methylimidazol-1-yl)ethyl]amino}piperidin-1-yl)phenyl]imidazolidin-idin-2-one<br>Reference # A0159 | | |
| 1-(2H-1,3-benzodioxol-5-ylmethyl)-4-[(3S)-1-(1H-imidazol-4-ylmethyl)piperidin-3-yl]piper-azine<br>Reference # A0161 | | |
| 6-(aminomethyl)-2-(3-{[4-(pyrazol-1-ylmethyl)piperidin-1-yl]methyl}phenyl)-3H-pyrimidin-4-one<br>Reference # A0162 | | |
| (4R)-N-[(6-chloroquinolin-2-yl)methyl]-1-(pyridin-2-yl)-4,5,6,7-tetrahydroindazol-4-amine<br>Reference # A0163 | | |
| (3R,4R)-4-[4-(pyridin-2-yl)piperazin-1-yl]-1-(pyridin-2-ylmethyl)piperidin-3-ol<br>Reference # A0164 | | |

-continued

| Compound Name | Structure | Score |
|---|---|---|
| 7-{[4-(4-acetylphenyl)piperazin-1-yl]methyl}pyrimido[2,1-b][1,3]thiazol-5-one<br>Reference # A0188 | | |
| 3-[(E)-{[3-(2,3-dihydro-1,4-benzodioxin-6-yl)-1-phenylpyrazol-4-yl]methylidene}amino]-8-methyl-diazaspiro[4.5]decane-2,4-dione<br>Reference # A0464 | | −40.20 |
| 1-(4-amino-1,2,5-oxadiazol-3-yl)-5-[4-(hydroxynitroso)phenyl]-N'-[(1E,2E)-3-phenylpropen-1-ylidene]-1,2,3-triazole-4-carbohydrazide<br>Reference # A0478 | | −33.55 |
| 3-({12-[4-(furan-2-ylcarbonyl)piperazin-l-yl]-8-oxo-15-oxa-14-azatetracyclo[7.6.1.0^{2,7}.0^{13,16}]hexadeca-1(16),2(7),3,5,9,11,13-heptaen-10-yl}amino)benzoic acid<br>Reference # A0506 | | −31.55 |
| 4-chloro-N-[(7S)-7-(4-fluorophenyl)-5-phenyl-4H,7H-[1,2,4]triazolo[1,5-a]pyrimidin-2-yl]benzenesulfonamide<br>Reference # A0452 | | −31.44 |
| (5S)-4-(2,3-dihydro-1,4-benzodioxin-6-ylcarbonyl)-5-(4-ethylphenyl)-3-hydroxy-1-(6-methyl-1,3-benzothiazol-2-yl)-5H-pyrrol-2-one<br>Reference # A0453 | | −31.25 |
| (5S)-1-(6-chloro-1,3-benzothiazol-2-yl)-4-(2,3-dihydro-1,4-benzodioxin-6-ylcarbonyl)-3-hydroxy-5-[4-(hydroxynitroso)phenyl]-5H-pyrrol-2-one<br>Reference # A0474 | | −30.74 |
| O-{[4-({4-[(2E)-2-[(3-fluorophenyl)methylidene]hydrazin-1-yl]-6-(morpholin-4-yl)-1,3,5-triazin-2-yl}amino)phenyl]nitroso}oxidanol<br>Reference # A0490 | | −30.26 |
| (2E)-3-(1,5-dimethyl-3-oxo-2-phenylpyrazol-4-yl)-5-[(3Z)-2-oxo-1H-indol-3-ylidene]-2-{2-[(3E)-2-oxo-1H-indol-3-ylidene]hydrazin-1-ylidene}-1,3-thiazolidin-4-one<br>Reference # A0491 | | −30.18 |
| 5-(5-{[(4Z)-5-oxo-1,3-diphenylpyrazol-4-ylidene]methyl}furan-2-yl)-2H-isoindole-1,3-dione<br>Reference # A0497 | | −30.18 |
| 5-[(6S)-5-benzyl-1H,4H,6H,7H-imidazo[4,5-c]pyridin-6-yl]-3-(pyridin-2-yl)-1,2,4-oxadiazole<br>Reference # A0204 | | −29.69 |
| 2-(hydroxynitroso)-6-[(1E)-(2-{4-[(4-methylphenyl)amino]-6-(morpholin-4-yl)-1,3,5-triazin-2-yl}hydrazin-1-ylidene)methyl]phenol<br>Reference # A0383 | | −29.17 |
| (7'S)-12'-({[(5E)-1-methyl-2,4,6-trioxo-1,3-diazinan-5-ylidene]methyl}amino)-5'-phenyl-2',5'-diazaspiro[1,5-diazinane-3,8'-tricyclo[8.4.0.0^{2,7}]tetradecane]-1(14'),10',12'-triene-2,4,6-trione<br>Reference # A0455 | | −28.98 |
| 4-[(10R,10aR)-7,7-dimethyl-9,11-dioxo-6H,8H,10H,10aH-indeno[1,2-b]quinolin-10-yl]phenyl 4-acetamidobenzenesulfonate<br>Reference # A0500 | | −28.71 |
| (5S)-1-(6-chloro-1,3-benzothiazol-2-yl)-4-(2,3-dihydro-1,4-benzodioxin-6-ylcarbonyl)-3-hydroxy-5-[3-(hydroxynitroso)phenyl]-5H-pyrrol-2-one<br>Reference # A0481 | | −28.43 |
| (5S)-4-(2,3-dihydro-1,4-benzodioxin-6-ylcarbonyl)-3-hydroxy-5-[3-(hydroxynitroso)phenyl]-1-(6-methyl-1,3- | | −27.96 |

| Compound Name | Structure | Score |
|---|---|---|
| benzothiazol-2-yl)-5H-pyrrol-2-one Reference # A0482 | | |
| N-cyclooctyl-3-[(4-fluorobenzene)sulfonamido]-4-[(1S,9R)-6-oxo-7,11-diazatricyclo[7.3.1.0^{2,7}]trideca-2,4-dien-11-yl]benzamide Reference # A0507 | | −27.83 |
| O-[(3-{[4,6-bis(1,2,3-benzotriazol-1-yl)-1,3,5-triazin-2-yl]amino}phenyl)nitroso]oxidanol Reference # A0484 | | −27.60 |
| N-[4-({5,7-diphenyl-[1,2,4]triazolo[1,5-a]pyrimidin-2-yl}sulfamoyl)phenyl]acetamide Reference # A0346 | | −27.16 |
| 3-({8-oxo-12-[4-(pyridin-2-yl)piperazin-1-yl]-15-oxa-14-azatetracyclo[7.6.1.0^{2,7}.0^{13,16}]hexadeca-1(16),2(7),3,5,9,11,13-heptaen-10-yl}amino)benzoic acid Reference # A0379 | | −26.67 |
| 1-(4-amino-1,2,5-oxadiazol-3-yl)-N'-[(1Z)-3,4-dihydro-2H-naphthalen-1-ylidene]-5-phenyl-1,2,3-triazole-4-carbohydrazide Reference # A0508 | | −25.98 |

Compounds specifically inhibiting the G12V mutant K-Ras protein conformations fall into two broad categories—those targeting the I-groove and the compounds that bind to the Y-groove. The former have a linear structure with abundant hydrophobic groups, such as phenyl rings, which provide the necessary rigidity and render the compound relatively flat. The latter are branched compounds designed to occupy the entire available volume of the Y-groove. They also consist mostly of aromatic rings and have multiple heteroatom-containing functional groups, which tend to improve aqueous solubility. Typically, there are few, if any, hydrogen bonds within the protein-ligand complexes, and most of the binding free energy is derived from hydrophobic interactions that are maximized by shape complementarity.

In order to confirm specificity of the discovered compounds toward the mutant forms of K-Ras, we have performed molecular docking of the selected ligands to the wild type K-Ras and scored the obtained bound orientations with MM-PBSA, following the same standard protocol. Nearly all scores were worse than those calculated for the ligand complexes with the mutant protein. The range of MM-PBSA scores was between −23.27 and −8.3, with the majority of compounds being at worse than −20. This further justifies the score cutoff for compound selection set at −25. Those few compounds that exhibited scores between −20 and −25 are bound to the wild type K-Ras in locations that are distant from the effector binding surface and are highly unlikely to influence normal function of the protein even if the binding in vivo is significant.

Additional compounds are identified using standard techniques well known to those of ordinary skill in the art. For example, high throughput screening of compounds that block or inhibit binding of mutant K-Ras proteins with known downstream proteins such as b-Raf, c-Raf (Raf-1) or PI 3-kinase. Alternatively, compound libraries can be generated using standard techniques well known to those of ordinary skill in the art using the compounds disclosed herein as starting material.

Exemplary Uses of Contemplated Compounds

The compounds identified by the methods described herein are useful for the treatment of cancers associated with mutant K-Ras activity. Approximately 33% of all human tumors express mutant Ras, these mutations often stabilize Ras in the GTP-bound (active) state. Mutations found in K-Ras associate strongly with pancreatic cancer (90%), biliary tract cancer (33%), colorectal cancer (32%), and lung cancer (20%), among others. Approximately 20-25% of all human tumors harbor an activating mutation in gene encoding K-Ras. Examples of cancer-associated mutations are found at glycine-12 (Gly12), Gly13, and glutamine-61 (Gln61), with Gly12 being the predominant site of mutagenesis (88%). Exemplary cancers associated with constitutive K-Ras activity include but are not limited to biliary tract, bladder, breast, cervix, endometrial, kidney, large intestine, liver, lung, melanoma, myeloid leukemia, ovarian, pancreas, and thyroid cancer.

The invention provides a pharmaceutical composition comprising described compounds and at least one pharmaceutically acceptable excipient or carrier. Methods of preparing such pharmaceutical compositions typically comprise the step of bringing into association a described compound with a carrier and, optionally, one or more accessory ingredients. The described compounds and/or pharmaceutical compositions comprising same may be formulated into pharmaceutically-acceptable dosage forms by conventional methods known to those of skill in the art. Typically, formulations are prepared by uniformly and intimately bringing into association a described compound with liquid carriers, or finely divided solid carriers, or both, and then, if necessary, shaping the product.

Pharmaceutical compositions of the present invention suitable for parenteral administration comprise one or more described compounds in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Pharmaceutical formulations of the described compounds suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a described compound as an active ingredient. A described compound may also be administered as a bolus, electuary or paste. A described compound may be administered transdermally (e.g., using a patch).

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular described compound employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the described compounds employed in the pharmaceutical composition at levels lower than that required in order to achieve the desired therapeutic effect and gradually increase the dosage until the desired effect is achieved.

In general, a suitable daily dose of a described compound will be that amount of the compound which is the lowest dose effective to produce a therapeutic effect. Such an effective dose will generally depend upon the factors described above. Generally, oral, intravenous, intracerebroventricular and subcutaneous doses of the described compounds for a patient, when used for the indicated effects, will range from about 1 mcg to about 5 mg per kilogram of body weight per hour. In other embodiments, the dose will range from about 5 mcg to about 2.5 mg per kilogram of body weight per hour. In further embodiments, the dose will range from about 5 mcg to about 1 mg per kilogram of body weight per hour.

If desired, the effective daily dose of a described compound may be administered as two, three, four, five, six or more sub-doses administered separately at appropriate intervals throughout the day, optionally, in unit dosage forms. In one embodiment, the described compound is administered as one dose per day. In further embodiments, the compound is administered continuously, as through intravenous or other routes. In other embodiments, the compound is administered less frequently than daily, such as every 2-3 days, in conjunction with dialysis treatment, weekly or less frequently.

These compounds may be administered to humans and other animals for therapy by any suitable route of administration. As used herein, the term "route" of administration is intended to include, but is not limited to subcutaneous injection, subcutaneous depot, intravenous injection, intravenous or subcutaneous infusion, intraocular injection, intradermal injection, intramuscular injection, intraperitoneal injection, intratracheal administration, intraadiposal administration, intraarticular administration, intrathecal administration, epidural administration, inhalation, intranasal administration, oral administration, sublingual administration, buccal administration, rectal administration, vaginal administration, intracisternal administration and topical administration, transdermal administration, or administration via local delivery (for example by catheter or stent). The described compounds may also be administered or co-administered in slow release dosage forms. The disclosed compounds have efficacy when administered systemically.

The following examples are offered to illustrate but not to limit the invention.

Example 1: Structural Analysis of Wild Type and Mutant K-Ras

The molecular dynamics program Amber 11 was used to analyze wild type and mutant K-Ras for structural differences. A series of simulations was run using the backbone conformation of the wild type K-Ras as the starting point. The G12V, G12D, and G12C mutant structures were obtained from that of the wild type protein by replacing the side chain of Gly12 using molecular graphics software. The Amber FF99SB force field was used to simulate mutant proteins in explicit water.

An initial premise for this study was that, given the different functional behavior exhibited by the mutant and wild type K-Ras proteins in vivo, there should be one or more structural difference evident between these proteins. Because no such differences were detected using crystallographic methodologies, molecular dynamic methods were selected to discover the structural reasons for such a difference. All simulations were started from the identical protein structures with the only exception of the mutation at the 12 position in the peptide chain. In this way, there was no pre-existing bias toward any particular protein conformation.

The simulations were run for over 100 nanoseconds of simulated time in each run, with noticeable differences between the G12V mutant, G12D mutant, G12C mutant, and the wild type K-Ras emerging after about first 10 nanoseconds. The remainder of the simulation served to confirm that the differences were not random fluctuations, but rather stable features due to the different side chains at the position 12.

Analysis of the resulting structures of the wild type and conformational forms of the mutant K-Ras has revealed major differences in the shape of the protein surface near the GTP γ-phosphate. The G12V mutant exists in solution as an ensemble of conformations, with two of them being the most predominant and accounting for at least 80% of the total simulated time. One of the forms is characterized by a deep groove in the surface that stretched for about 16 Å from Asp92 to Ile36. This groove in the mutant K-Ras appears to have originated from the dramatic change in the position of Gln61 side chain, which swings away from the bulky isopropyl group of the Val12 in the mutant K-Ras. The other conformer of the mutant K-Ras features a branched variant of the surface groove termed the Y-groove, which refers to the geometry of this surface feature. Both openings of the Y-groove are on the interaction surface of K-Ras with PI3K and Raf. The wild type protein has no such features, and apparently has a shallow groove that runs in perpendicular direction from Lys117 to Tyr64. In the wild type protein, the Gln61 points toward the glycine at the 12 position and is generally located in proximity of the GTP γ-phosphate.

The I-groove on the surface of K-Ras spans the following set of residues: Glu91, Asp92, Tyr96, Ala11, Gly60, Ala59, Thr35, Pro34, and Ile36. It is also flanked by side chains of the following: Gln61, Lys88, Val12, Glu62, Tyr32 and the γ-phosphate of the GTP. The Y-groove is defined by the following residues: Asp92, Ala11, Gln61, Glu62, Gly60, Ala59, Thr35, Arg68, Thr58, Tyr71. The side chain of Ile36 serves as the divider between the two branches of the Y-groove.

The overall shape and size of both grooves makes them capable of accommodating an organic drug-like compound. In addition, the grooves open near Ile36 and Pro34, the contact residues important for formation of the complex with RAF and p110 subunit of PI3K. If this interaction is inhibited by a compound that targets the groove, downstream signaling by mutant K-Ras will be disrupted. At the same time, the wild type protein will be unaffected.

Example 2: In Vitro Cell Death Assays

The validity of the current computational approach is confirmed by testing the ability of the candidate compounds to inhibit the function of constitutively-active mutant K-Ras. Inhibition of mutant K-Ras expression has previously been shown to specifically activate the demise of mutant expressing cancer cells (Zhu et al., Canc. Biol. & Ther., 2006; Chen et al., World J. Gastro, 2005; Zhang et al., Canc. Res., 2006). Thus the following methodology is used to confirm the predicted efficacy of the identified compounds.

Protocol for Cell Death Assessment:

Screening compounds that are predicted to selectively target K-Ras mutant cells will comprise of assessment of cell death in human cancer cells bearing activating K-Ras G12V mutations (e.g., human colon SW480) and counter assessment of viability in K-Ras WT human cells (e.g., HT29, 293, etc.). SW480 and HT29 cells are both propagated at 37° C./5% $CO_2$ and in RPMI+10% fetal bovine serum (FBS) and DMEM+10% FBS, respectively. Upon plating cells in microtiter plates, compounds are supplemented at various concentrations and viability is assessed within 24-72 hrs by manual or automated (Countess (Invitrogen)) trypan blue cytometry.

Cell death analysis of candidate compound A0383 in K-Ras wild type expressing 293 cells did not uncover unspecific toxicity ($IC_{50}$>100 μM) (FIG. 6B).

Protocol for Assessment of Alterations in Protein Biochemistry:

Compounds predicted to interfere with the function of mutant K-Ras will impact downstream signaling mechanisms, including though not limited to the K-Ras/PI3K/Akt/mTOR and K-Ras/Raf/MEK/ERK pathways. Screening for inhibition of constitutive activation of these pathways will consist of determining the phosphorylation patterns indicative of activation of downstream effector proteins. Specifically, the phosphorylation events apparent in Akt and MEK 1 or 2 kinases are assessed for the impact of compounds in the K-Ras/PI3K/Akt/mTOR and K-Ras/Raf/MEK/ERK pathways, respectively. Briefly, wild type and mutant K-Ras expressing cells are treated with compounds for 24-48 hrs, cells collected and lysed, and proteins separated via standard electrophoresis techniques. Alternatively, 293 cells overexpressing WT, G12V, G12D, G12C, or G13 are treated with compounds for 24-48 hours, cells collected and lysed, and proteins separated via standard electrophoresis. Alternatively, lysed cells are subjected to ultra-sensitive immunoassays. Finally, immunoreactivity with phospho-specific antibodies to Akt and MEK1/2 determines impact on the pathways mentioned above.

Immunoassay with candidate compound A0383 showed significant reduction in the phosphorylation and activation of the downstream Ras signaling protein MEK, which is phosphorylated by the Ras effector protein Raf (FIG. 6A).

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. A mixture comprising:

a K-Ras protein (SEQ ID NO:1) with a G12V substitution, wherein the K-Ras protein with the G12V substitution has a first and a second mutant conformation, wherein the first mutant conformation has a first mutant groove defined by Glu91, Asp92, Tyr96, Ala11, Gly60, Ala59, Thr35, Pro34, and Ile36;

wherein the second mutant conformation has a second mutant groove outlined by Asp92, Ala11, Gln61, Glu62, Gly60, Ala59, Thr35, Arg68, Thr58, and Tyr71; and a compound bound to the first or second groove, wherein the compound is 2-(hydroxynitroso)-6-[(1E)-(2-{4-[(4-methylphenyl)amino]-6-(morpholin-4-yl)-1,3,5-triazin-2-yl}hydrazine-1-ylidene)methyl] phenol) (A0383).

* * * * *